US005446369A

United States Patent [19]

Byrne et al.

[11] Patent Number: 5,446,369
[45] Date of Patent: Aug. 29, 1995

[54] CONTINUOUS, AUTOMATIC AND REMOTE MONITORING OF CORROSION

[75] Inventors: Mark T. Byrne, Loveland; Kenneth L. Kimes, Mt. Gilead; John T. Stropki, Westerville, all of Ohio

[73] Assignee: Battelle Memorial Institute, Columbus, Ohio

[21] Appl. No.: 134,292

[22] Filed: Oct. 8, 1993

Related U.S. Application Data

[63] Continuation-in-part of Ser. No. 958,805, Oct. 9, 1992, abandoned.

[51] Int. Cl.6 .............................................. G01N 27/20
[52] U.S. Cl. .................................... 324/71.2; 324/71.1; 324/700; 204/404; 422/53
[58] Field of Search .................. 324/425, 71.1, 71.2, 324/700; 73/86; 204/404, 153.11; 422/53

[56] References Cited

U.S. PATENT DOCUMENTS

| | | |
|---|---|---|
| 2,824,283 | 2/1958 | Ellison . |
| 2,834,858 | 5/1958 | Schaschl . |
| 3,047,847 | 7/1962 | Marsh et al. ............... 324/700 X |
| 3,067,386 | 12/1962 | Freedman .................. 324/700 X |
| 3,936,737 | 2/1976 | Jefferies, Sr. ............... 324/700 |
| 4,019,133 | 4/1977 | Manley et al. ............... 324/700 |
| 4,217,544 | 8/1980 | Schmidt ..................... 324/700 X |
| 4,238,298 | 12/1980 | Tsuru et al. ................. 204/1 T |

FOREIGN PATENT DOCUMENTS

| | | | |
|---|---|---|---|
| 2919642 | 4/1980 | Germany .................. C25F 7/00 |
| 2080537 | 7/1980 | United Kingdom ........ G01N 17/00 |
| 2064124 | 6/1981 | United Kingdom ........ G01N 17/00 |
| 9106854 | 5/1991 | WIPO ..................... G01N 33/24 |

OTHER PUBLICATIONS

Measuring Corrosion: Coupons and Electrical Resistance Probes Krisher, A. S., Mater Protect V 4, No. 10, Oct. 1965, pp. 8-10.

Use of Weight Loss Coupons and Electrical Resistnace Probes in Atmospheric Corrosion Tests, McKenzie & Vassie, Br. Corros. J., 1985, vol. 20, No. 3.

*Primary Examiner*—Kenneth A. Wieder
*Assistant Examiner*—Glenn W. Brown
*Attorney, Agent, or Firm*—Barry S. Bissell

[57] ABSTRACT

The corrosion monitor system facilitates the detection and monitoring of material corrosion in remote areas. Sensors, which react to a corrosive environment similar to the material to be monitored, are placed in isolated areas and connected to a central control system via shielded cables. The system consists of a controller board, multiple dual preamp boards, a battery pack, sensors, and corresponding cables. The controller board consists of a microcontroller, memory, data conversion, and other control circuits. The dual preamp boards contain multiple precision instrumentation amplifiers, filtering, and voltage conversion circuits. The system operates on the principal that corrosion of a metallic conductor will cause a corresponding increase in the cross-sectional electrical resistance of that conductor. This change in resistance can be detected and monitored by passing a known constant current through the conductor and comparing the voltage across the conductor with that of a controlled reference conductor. The reference conductor is not exposed to the corrosive environment. As the sample conductor corrodes, small increases in the voltage across the element are measured with respect to the reference material. The resultant signals are multiplied and filtered to a detectable level and processed by the controller as data points stored in memory.

24 Claims, 6 Drawing Sheets

CONTINUOUS, AUTOMATIC AND REMOTE MONITORING OF CORROSION

This invention was made with Government support under Contract No. DLA900-83-C-1744 awarded by the United States Department of the Air Force. The Govenment has certain rights in this invention.

This is a continuation-in-part of application Ser. No. 07/958,805, filed Oct. 9, 1992, now abandoned.

FIELD OF THE INVENTION

This invention relates to corrosion monitoring and in particular to a method and apparatus for the continuous, automatic and remote monitoring of potentially corrosive environments in difficult to reach places.

BACKGROUND OF THE INVENTION

Prior attempts at corrosion monitoring used manual instrumentation to measure resistance changes at each site. This instrumentation had to be manually balanced in order to achieve the sensitivity necessary to detect small resistance changes. Although such conventional techniques are relatively satisfactory where there is adequate space and time for their use, there are many corrosive environments that need continuous or frequent corrosion monitoring and/or are relatively inaccessible making it difficult or impossible to use conventional techniques.

With aging fleets of aircraft in use both in the military and commercial sectors, corrosion of body and support component surfaces in secluded areas is of crucial concern. Current efforts to detect corrosion on aircraft surfaces consist of visual inspection of the accessible surfaces on a routine basis. Aircraft surfaces that are difficult to access often receive less attention and may not be inspected until aircraft overhaul, which typically occurs every five years. The overhaul process involves the disassembly of the body of the aircraft. The body panels are removed and inspected leaving only a frame skeleton. This process has often revealed corrosion problems in many of the remote areas of the dismantled aircraft. Potential safety concerns prompt the need for continuous corrosion detection capabilities in secluded aircraft compartments.

SUMMARY OF THE INVENTION

A method and apparatus has now been devised wherein corrosion sensors may be positioned in difficult to access and confined spaces having potentially corrosive environments to provide periodic automated testing, reporting and/or recording to positions remote to such spaces.

The instant corrosion monitor system consists of sensors, preamplifiers, a controller and a battery pack. The system can support a number of sensors, each with dedicated preamplifiers, to monitor many sites in a given installation. The preamplifiers, controller and battery-pack may be packaged as a single instrumentation unit. Sensors can be attached to the instrumentation via cables (advantageously up to 100 ft long, or longer). Each sensor may combine a thermistor and two corrosion sensing elements. The sensor elements are connected as a resistive half-bridge, or its equivalent, with a reference and an exposed element. The instrumentation system passes a forward current through the sensor and measures the voltage differential between the exposed and reference elements in order to determine corrosion activity. Measurement of sensor temperature allows the raw corrosion activity data to be temperature compensated.

The reference and exposed sensor elements may be fabricated with the same material as the structure of interest, thus an environment that causes corrosion in the structure under observation would also cause corrosion in the exposed sensor element. The reference element is sealed to prevent corrosion from changing its resistance. Sensor corrosion manifests itself as a change in the resistivity of the sensor element. Typical corrosion rates in aircraft produce resistance changes on the order of hundreds of microohms or less per year. A fundamental design problem in the development of a corrosion monitor system for such applications is the detection of small changes in sensor resistance over time and at the same time satisfy package size and low power consumption constraints. The expected corrosion changes result in differential voltage levels at the preamplifier input on the order of tens of microvolts.

The present system is automatic in the sense that no operator is needed. It can be installed with the sensors and left in place to record resistance changes on a periodic basis over an extended period of time. In the demonstration system corrosion measurements are made once a day. The measurement rate can be changed to meet the requirements of a specific application. When the instrument is not taking data it may be made to shut down to extend battery life. Periodically, the data stored by the corrosion monitoring system can be transferred to an external computer for post-processing and interpretation.

A particularly advantageous feature that may be incorporated into the present system is a preamplifier subsystem. To meet the criteria of the present need (i.e. a light compact system to fit on aircraft) small, low-noise, low-power preamplifiers were devised to convert the very small sensor output to a usable signal.

The corrosion monitor system of the present invention has been found to be particularly useful to aid in the evaluation of anti-corrosion surface treatments. Typically, two corrosion sensors are placed together in the area to be evaluated. One of the sensors contains a bare test conductor. The other sensor is treated with the same anti-corrosive coating that is used on the parts or surfaces to be protected from the corrosive environment, such as the section of the aircraft in which it would be used. The bare sensor then yields data that shows how the local surfaces to be tested, such as the aircraft surfaces, would react if they were untreated. The coated sensor demonstrates the surface treatment's relative capability in preventing premature corrosion. Together, the two sensors help to determine the overall effectiveness of surface coatings.

DESCRIPTION OF THE PREFERRED EMBODIMENTS

Corrosion monitor sensors of the type employed in conjunction with the method and apparatus of the present invention are well known in the art. A sensor that may be employed in conjunction with the present invention is described in U.S. Pat. No. 2,834,858 to E. Schaschl. The sensing material and its physical parameters depends on the local surfaces to be evaluated and the corrosiveness of their environment. The sensor operates on the principal that corrosion of a metallic conductor will cause a corresponding increase in the cross-sectional electrical resistance of that conductor. This increase in resistance is due to actual material loss during the corrosion of the metallic surface. This material reduction is most noticeable in the appearance of small holes on the surface known as pitting. As conductive material is removed by corrosion, electron flow is limited due to reduced electrical path. This causes an increase in the electrical resistance of the conductor similar to the way that pinching a hose would increase the impedance to water flow through the hose. The resultant rise in electrical resistance in response to material corrosion is converted and measured by the monitor system. The electrical resistance of the test conductor is read as a voltage across the conductor by passing a constant (i.e. direct) current through it.

Figure 1:
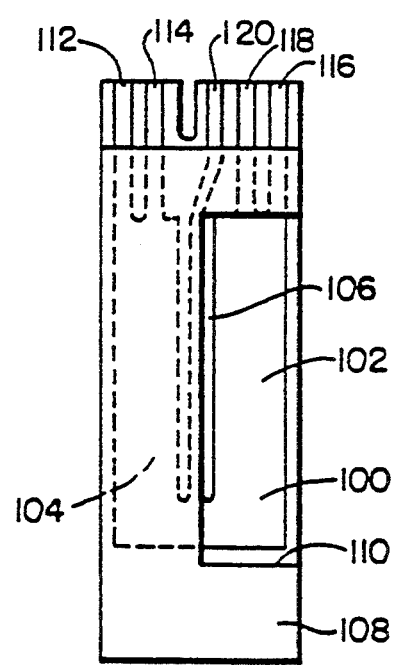
FIG. 1 is a plan view of a sample test probe used in the method and apparatus of the present invention.

The test probe of FIG. 1 comprises a coupon 100 made of the test material. This material is the same as that of the structural materials to be monitored. Such material is generally an aluminum alloy where the monitoring is for aircraft. Coupon 100 is divided into two halves 102 and 104 that are separated by a spacing channel 106. Coupon 100 is enveloped in a protective plastic envelope or coating 108 that covers and protects from corrosion all of the surfaces of coupon 100 (back and front) except one surface of half 102 that is exposed by a window 110 provided in envelope 108. Half 104 of coupon 100 is covered on all surfaces by the protective envelope or coating 108. Leads 112 and 114 are connected to coupon half 104 and extend from the front surface of envelope 108 (the back surface of envelope 108 extends beyond the front surface). Leads 116 and 118 are similarly attached to coupon half 102. A single lead 120 extends from the bottom of the spacing channel 106 between halves 102 and 104 to extend beyond the protective envelope 108.

In operation, coupon half 102 is the test conductor and half 104 is the reference conductor. Lead 116 may be attached to power source 109 of the system of FIG. 2, lead 118 may be connected to contact 111, lead 112 may go to ground, lead 114 may be connected to contact 115 and lead 120 may be attached to contact 121. By placing the coupon in a monitoring position so that the corrosive effects of the environment will affect the exposed surface of coupon 102 in the same manner as the adjacent structural members and monitoring in the manner described in conjunction with the system of FIG. 2 it is possible to achieve the goals set forth for the invention.

Figure 2:
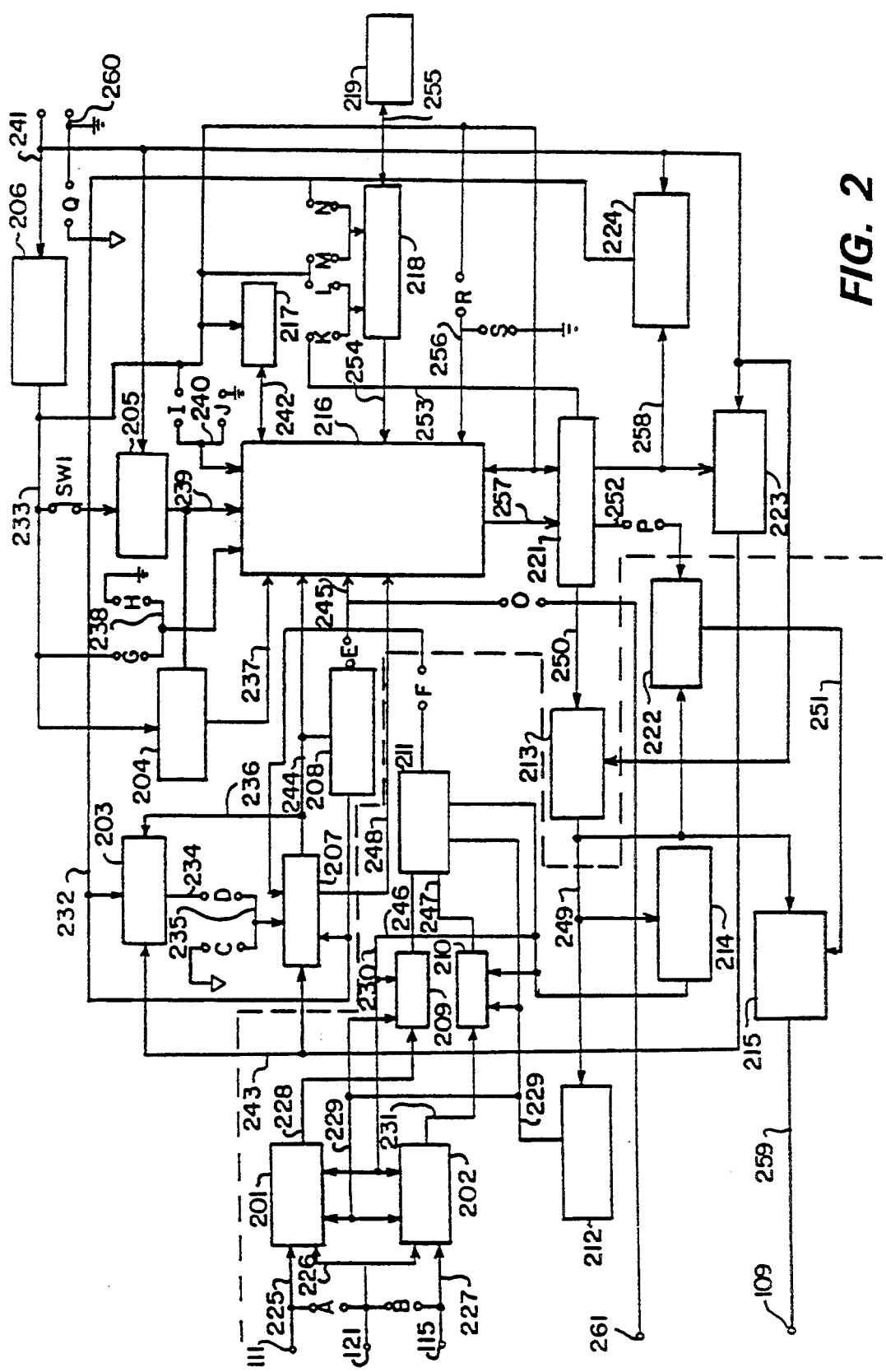
FIG. 2 is a schematic circuit block diagram of a dc monitoring system embodying the features of the present invention.

FIG. 2 of the drawing shows the major system electronic components and circuits. Both the controller and dual preamp circuits are covered by this diagram. The principal circuits and signals are numbered and the circuit board jumpers are lettered for reference in the circuit descriptions. Note that the alphanumeric designations used on this block diagram are to serve as references only and are not derived from actual part numbers or jumper letter identifiers. The jumper designations called out in the initialization and download procedures described later in this text are actual circuit jumper designators and differ from the references shown in the block diagram and listed in the circuit descriptions.

Each sensing probe contains two conductors, test and reference, which are monitored by the system. The reference conductor is sealed to protect it from the corrosive environment. The test conductor is exposed to the environment for open air testing or the application of any representative coatings to be evaluated. Since the percentage change in the resistance of the test conductor is extremely small, a comparison method is used which measures the impedance of the test conductor with respect to the reference conductor. The system monitors relative changes in the electrical resistance of the test conductor by comparing the voltage across it to that of the reference conductor. This comparison method enables the system to detect very small incremental changes (micro-ohms) in the resistance of the test conductor. This method also adds some built-in compensation for the effects of ambient temperature on the resistance of the material as the reference and test conductors are equally affected. The probes also include built-in thermistors for local temperature indication. The probes are connected to the main system compartment via seven conductor plus ground shielded 24AWG cables. Further details concerning the test probe circuit interface are contained in the preamp circuit description.

Due to induced thermal effects, careful consideration must be made to determine how long to run the 100 mA current through the probe conductors before data is acquired. The data is not taken instantly so that the current has time to stabilize. But, if given too much time, the data will be obscured by the heating up of the reference conductor with respect to the test conductor. Although both conductors are heated by the 100 mA current, the reference conductor, being sealed up from the local atmosphere, cools less efficiently than the exposed test conductor. Given enough time, this relative heating of the reference conductor will cause its resistance to increase with respect to that of the test conductor. This causes erroneous negative data points to be acquired by the system. To avoid this problem, probes which utilize different metals of various thicknesses are evaluated with respect to their thermal response to the current which is passed through them. Two seconds wait time proved to be adequate for 4 mil and 8 mil thick aluminum probes.

It is well known to those skilled in the art that the responses of any electronic or electricity dependant device will vary to at least some degree in accordance to the temperature to which it is subjected during operation. Such effect may be negligible or may be of some consequence where comparative measurements are such as in the present instance. One solution to the problem is to simply take temperature measurements in the vicinity of the operating devices with conventional instruments such as a thermometer and calculate appropriate compensations in the output of the device since the temperature effect on such components is known or may be easily developed. This is easily accomplished in conjunction with the operation of the systems of the present invention because its reduction to practice has been essentially accomplished with conventional devices such as described below and the temperature effect on such devices is known.

Commercially available devices such as those employed in the system of the present invention may be provided with built in temperature compensating devices called thermistors which automatically or which may be made to effect such temperature compensations. Such devices may vary in the manner by which they function but generally function in accordance with the description found in the publication *OMEGA Temperature Handbook*, 1991, pp Z24 & 25 which is incorporated herein and made a part of this specification.

Thermistors or the application of temperature compensation are well know in the art and are not claimed as a part of the present invention since viable results may be achieved with either the application of a commercially available thermistor device or conventional temperature measuring instruments. Such technology is described herein to assure the best mode in practicing the present invention has been made available to those of ordinary skill in the art.

The dual preamp board (see FIG. 2) provides the circuitry to interface two test probes to the controller board. This circuitry converts very small sample sensor resistance changes into analog voltages and interfaces these signals to the controller board analog to digital converter (A/D 211). During data acquisition, 100 mA of current 259 is supplied to each of the probes by a constant current source circuit 215. The resultant voltage across the test conductor 225, 226 is input to an instrumentation amplifier 201. The voltage across the reference conductor 226, 227 is also input to an instrumentation amplifier 202. These first stage amplifiers amplify the conductor voltages by approximately a factor of 1000. The resultant output signals 228, 231 are processed through dual cascaded non-inverting low pass filters 209, 210 which also amplify the signals by a factor of about 2.5. The filter outputs 246, 247 are input to a final amplifier stage 211 which yields the difference between the two signals amplified by a factor of 20. The preamp circuit provides an overall gain of 50,000 to the voltage difference between the test and reference conductors. The final output is then routed to a 12 bit A/D converter 207 on the controller circuit board. Each of the preamp boards contains two preamp circuits and as many as four preamp boards may be used per system under current configuration. This creates the potential for as many as eight channels of information to be input to the A/D converter 207. Slight circuit modifications would allow even more input channels if necessary. Jumper F represents one of eight jumpers per dual preamp board that directs the analog output signal to its corresponding input channel 236 into the A/D converter 207.

Each probe also provides a temperature input 261 from a built-in thermistor (not shown). The eight temperature inputs are routed to the controller circuit board in the same manner as that described above. Jumper O represents one of the eight jumpers per preamp board that directs the analog temperature, signal to its corresponding input channel 245 into the microcontroller's onboard A/D converter. The electrical resistance of the thermistor varies with temperature. The thermistor is connected into a two-resistor (10 K$\Omega$ to +5 V and 10 K$\Omega$ to ground) voltage divider in parallel to the bottom resistor. The varying thermistor resistance causes the parallel leg resistance ($R_{Thermistor}$ & 10 K$\Omega$) to vary along with the leg voltage. This analog voltage level is read and stored by the microcontroller.

Power 249 is provided to the dual preamp board by a high-side driver circuit 213 on the controller board. This power input is connected to the preamp voltage converter 212, voltage regulator 214, constant current source 215 and current enable circuit 222. The preamp voltage converter 212 converts the 12 volts supplied by the high-side drive circuit 213 to a −5 volt supply 229 for the instrumentation amplifiers 201 and 202, the filter circuits 209 and 210, and the instrumentation amplifier 211. The preamp voltage regulator 214 converts the 12 volt input from the controller board to a +5 volt supply 230 for the dual preamp board (i.e. amplifiers 201 and 202, filter circuits 209 and 210 and amplifier 211). The preamp current circuit 215 converts the 12 volt input into a 100 mA constant current source 259 which is run through the test probes. This source is directly controlled by a signal 251 from the enable circuit 222 which is driven by the controller board.

Jumper P represents one of four jumpers per preamp board that directs the current control output signal 252 from the controller board. The current supplied to the test probe represents the majority of the power consumed by the corrosion monitor system. Since the data from the A/D converter is read sequentially, each preamp board is enabled and disabled consecutively. In this manner no two boards are energized simultaneously, maximum battery current is minimized, and battery life is extended.

Jumpers A and B are used to simulate the connection of an external test probe for each Channel by shorting the inputs to the first stage amplifiers. These jumpers are used during board testing and tuning which is further described later. The two channels on each preamp board connect to the controller board via a 24 pin inline connector. To conserve space, the controller board and up to four dual preamp boards are stacked vertically and utilize this common connector for signal routing. Jumpers F, O and P represent three jumper sets per channel of each preamp board. These jumper sets are used to determine which of the eight potential channels of data and control each preamp circuit represents.

The controller board contains the main control circuitry for the corrosion monitor system. The controller board enables and disables the power and constant current source for each of the preamp boards and extracts data from them in a sequential manner at regular time intervals. The controller board also provides all user interface, which includes system setup, data retrieval through an RS-232 serial port 219, and system reset control via switch SW1. Each line of corrosion probe output data forms one of eight analog inputs 236 to the 12 bit A/D converter 207. The resultant digital output signal 248 is clocked into the microcontroller 216 (hereafter also referred to as the microprocessor). Jumpers C and D are used to set the input range 235 of the A/D converter. Jumper C sets the analog input range at 0 to +2.5 volts. Jumper D sets the input range at −2.5 to +2.5 volts. The jumper is typically placed in position C since corrosion causes a positive output as the voltage across the test conductor is increased with respect to that of the reference conductor.

The controller board circuitry includes a precision reference 208 which provides +2.5 volts 244 to the controller 216, A/D converter 207, and voltage inverter circuit 203. This reference also has a built-in temperature sensing capability. Jumper E represents one of eight jumper positions which will allow the user to connect this temperature output into any one of the controller's A/D converter input lines in place of the corresponding input 245 from the preamp board. This allows monitoring of the temperature inside the system enclosure during operation. Since the test probes are typically placed in pairs to help evaluate coating materials, it is only necessary to use one temperature output for each pair of probes. If one of the four extra temperature input jumpers is disconnected, the controller board temperature input can be jumped into the vacant input channel.

A decoder/latch 221 is used by the microcontroller 216 to manage several on-board functions. Five signal lines 257 from the microprocessor 216 are used to control the decoder. The current enable output represents four signals 252 that are routed to the preamp boards to turn on the current source for the test probes consecutively. Another decoder output 250 controls the high-side driver 213 which supplies power to all of the preamp boards. A third control output 258 from the decoder 221 shuts down the negative voltage converter 223 and one of the voltage regulators 224. The final decoder output 253 connects to jumper K, which allows the microprocessor to control the RS-232 port.

The controller board contains several microprocessor support circuits which include the real-time clock 204, controller reset/watchdog 205, RS-232, and memory 217. The real-time clock 204 is set to run at 32.768 KHz and provides full clock and calendar features. Multiple signals 237 between the real-time clock and controller provide time and date information to wake up the controller at a preset interval.

The reset/watchdog circuit 205 provides a reset output 239 to the microprocessor and real time clock 204 for power-up, power-down and brownout conditions. This circuit also provides a power fail warning input 239 to the controller 216 as it monitors the battery input voltage level 241. The power fail circuit uses a resistive divider with the watchdog's 205 interval 1.3 volt threshold to indicate a low battery status when the battery voltage drops below 6.5 volts.

The RS-232 circuit 218 transmits/receives serial data to/from the microprocessor 216 through two data lines 254. Data is transmitted to and from the corrosion monitor system via a serial port 219 across two data lines 255. The controller board contains a right angle D-9 serial connector (serial port 219) for interface to an external computer. The RS-232 circuit includes two sets of jumpers for changeable control. Jumpers M and N allow choice of +5 volt supplies to the circuit. Position M connects the circuit to the output 233 of the voltage regulator 206 which is always on. Jumper position N connects to the regulator 224 which can be shut off by the controller 216. The jumper is typically placed in position N so that the RS-232 circuit can be disabled to eliminate quiescent current consumption. Jumpers K and L connect to the enable input of the RS-232 circuit. Position K is the normal operating position as it allows control 253 of the serial port by the microprocessor. Position L connects +5 volts to enable the RS-232 circuit. This position is used during the data retrieval process described later.

The corrosion monitor system program software is stored on a 32K byte EEPROM memory circuit 217 which connects to the controller through multiple ports 242. This memory stores the program software and all of the data that is captured by the system. The microprocessor's on-board memory is used only to store the software which writes data to the external EEPROM 217. No data or other program information is stored in the controller memory.

The microprocessor 216 is connected to three pairs of jumpers to control various modes of operation for the system. Two of these pairs (jumpers G, H, I, J) control the operating mode inputs 238 and 240 of the controller with respect to external memory recognition. Both jumpers are placed in the +5 volt position (G and I) which places the controller in the expanded multiplexed mode and indicates the use of an external memory circuit. The third pair of jumpers (R and S) control the input 256 to one data line of the microprocessor's parallel port. These jumpers determine the system data acquisition interval. Position S sets the normal operating or 24 hour mode which causes the system to awake and take data once per day. Position R enables the debug mode and causes the system to take data approximately every two minutes. The debug mode is typically used during initial setup to verify system functionality and probe output data.

Power to the controller board comes directly from a lithium battery pack. The battery ground line 260 is connected to the digital ground. Jumper Q connects the analog and digital grounds together and is in place during normal operation. The battery input 241 connects to the voltage converter circuit 223, two voltage regulators 224 and 206, the reset/watchdog circuit 205, and a high-side driver 213. The voltage converter circuit 223 provides a −5 volt supply 243 for the voltage inverter 203 and 12 bit A/D 207. The first voltage regulator 206 is always enabled and provides +5 volts 233 to the real-time clock 204, EEPROM 217, microprocessor 216, and decoder/latch 221, as well as jumpers G, I, L, M, and R. This five volt supply is also connected to the reset/watchdog circuit 205 via normally closed momentary switch SW1, which provides system reset when temporarily opened. A second +5 volt regulator 224 is identical to the first except that it can be shut off by the controller. This regulator supplies power 232 to the +2.5 V reference 208, 12 bit A/D, voltage inverter circuit 203, and jumper position N. The voltage inverter circuit 203 provides −2.5 volts 234 for the A/D input range setting as described earlier.

The amount of current flow required for effecting the method of the present invention depends, of course, on the specific requirements and parameters of the system being tested. The primary requirement is that it be a constant dc current. Such current must be of low amperage to conserve the battery utilized since for many applications such as aircraft a satisfactory non-battery electrical source is not available. Preferably such amperage will not exceed about 0.5 amperes. Particular success has been achieved with 100 mA. The voltages applied to all of the various components and subcircuits, such as the regulators and inverters, may also, of course, vary.

Amplification of the sensor elements voltage for measurement is of particular importance for the low current densities (preferably no greater than about 0.5 amperes) of the present system. As shown above particular success has been achieved when employing 100 mA current with amplifications of 50,000. However, optimum amplification will vary in accordance with the exact current input. Generally, it will not be possible to detect voltage increases that show significant corrosion of an element where such total amplification is less than about 20,000. Where such amplifications exceed about 60,000 it is not possible to effectively determine the voltage increases due to static interference which accompanies such low current density amplifications and which may not be adequately filtered from the system.

The above described corrosion monitor is programmed to measure and record sensor signals at predetermined intervals. Procedures for downloading corrosion data from the corrosion monitor have been demonstrated using a special communications program within the Smarterm 240 software package. This program allows all "raw" voltage signals emitted from the corrosion sensors and stored within the data acquisition system to be transferred onto a magnetic diskette via a laptop computer. Once transferred, a second routine in the program allows the user to initialize the corrosion monitor to begin data collection procedures.

All sensor (voltage) data is input into Lotus 1-2-3 and subsequently stored on magnetic diskettes. The data is then automatically normalized with respect to the resolution or sensitivity of the system, and converted into real-time corrosion measurements. A time-dependent statistical analysis is performed on the measurements recorded by the individual sensors. The software package used to perform these analyses is Table Curve. Once analyzed, a comparative evaluation is performed on all measurements to determine differences and/or similarities in the trends recorded for sensors installed in identical areas on aircraft.

In-situ corrosion rates are calculated for all sensors by measuring the relative change in response signals (increase in signal strength denotes corrosion) noted for the individual sensors as a function of exposure time. Numerical constants related to the composition and thickness of the sensor's "test element" as well as yearly conversion factors are included in these calculations. Post-analysis presentation of all sensor data is set-up and displayed using Lotus PrintGraph software.

The corrosion monitor system operation is fully automated and should not require service, once set up, until battery pack replacement (4-6 months). Before the system is put into place, probes are paired with preamp boards for board tuning. This tuning process sets the data starting point at zero as there should be no corrosion on the test probes at this time. The tuning process includes adjusting the amplifier offsets such that the output of each stage and the final data output are set to zero. After all of the preamp boards are tuned with respect to certain probes, the system is put into place and the probes are connected to their respective board channels. The system is then initialized through the following procedure:

Procedure For Setting Up Corrosion Monitor For Data Collection:
  Connect serial cable between serial ports of the laptop PC and the Corrosion Monitor
  Boot up laptop PC
  Insert Smarterm 240 diskette
  Switch to the A drive via "A:"
  Invoke Smarterm via the command "ST240"
  Select setup configuration 7 (RUST)
  Make sure that the following jumpers are installed: JBAT, JB, JC, JE, JG, JL, JM, JU
  Connect the battery power to the controller board (observe polarity)
  Enter to get the prompt from the Corrosion Monitor
  Enter "R" to select the RUN option
  Enter the noise factor X as 5
  Enter the present hour and minute in 24 hour mode (remember spaces)
  Enter the wakeup hour and minute in 24 hour mode (remember spaces)
  Wait for wakeup in debug mode and verify that data is correct
  Disconnect battery power
  Move jumper JU to JV to configure for 24 hour mode
  Enter the file capture mode by typing "Alt-C"
  Change the capture filename by typing "F", then type a unique filename with "a:" as a prefix (Example: "A:SETUP3.DAT")
  Press the <Enter> key to begin file capture
  Reconnect the battery power to the controller board (observe polarity)
  Enter to get the prompt from the Corrosion Monitor
  Enter "R" to select the RUN option
  Enter the noise factor X as 5
  Enter the present hour and minute in 24 hour mode (remember spaces)
  Enter the wakeup hour and minute in 24 hour mode (remember spaces)
  Wait for the first wakeup (if feasible) in 24 hour mode and verify that data is correct
  Move jumper JL to JK to shut off serial port
  Once the data has printed to screen, type "Alt-C" again to exit the capture mode
  Type "Alt-X" to exit Smarterm 240

The corrosion monitor system will acquire data once per day (for up to 200 days) after initialization and will store the data in EEPROM memory. To minimize battery current drain, the microprocessor remains in an inactive or "sleep" state when no data is being acquired. At a preset time each day, indicated by the real-time clock, the controller is "awakened" by an interrupt to set the program in motion. The controller then applies power to the preamp boards. Power to the preamp boards is left on for 15 minutes before any data is collected to ensure that the supply voltages have reached equilibrium. After the 15 minute warm-up time the 100 mA current source is enabled on the first preamp board. The current is passed through the two test probes and a data point is received, converted, and stored in memory. Temperature data is also collected and stored at this time. Once this data is collected, the 100 mA current source for the first board is disabled. The current source for the second board is then enabled and the process is repeated. After corrosion and temperature data has been collected and stored for all of the test probes (up to eight), the microprocessor returns to its "sleep" mode until the following day.

If it is not needed earlier, the corrosion monitor data should be retrieved at the time that the battery pack is replaced. The procedure for downloading the data is as follows:

Procedure For Dumping Data From Corrosion Monitor:
  Connect serial cable between serial ports of the laptop PC and the Corrosion Monitor
  Boot up laptop PC
  Insert the Smarterm 240 diskette
  Switch to the A drive via "A:"
  Invoke Smarterm via the command "ST240"
  Select setup configuration 7 (RUST)

Enter the file capture mode by typing "Alt-C"
Change the capture filename by typing "F", then type a unique filename with "a:" as a prefix (Example: "A:WROBINS3.DAT")
Press the <Enter> key to begin file capture
Reset the Corrosion Monitor via the reset switch
Enter a carriage return to get the prompt from the Corrosion Monitor
Enter "D" to select the DUMP option
Once all of the data has dumped, type "Alt-C" again to exit the capture mode
Type "Alt-X" to exit Smarterm 240
Verify that the data was captured correctly by viewing the file via the command "TYPE 'filename'"at the A: prompt
If the file does not exist or it's contents look suspicious, repeat all of the above steps.

The corrosion monitoring system as represented by the components of the drawing consist of, and function in accordance with well known electrical and electronic principles. The function of the various components and their replacement with equivalent sub circuits are well within the skill of those of ordinary competence in the technology. The following list of commercially available components are those that have been used to demonstrate the invention:

| Drawing Nos. | Component Description & Manufacturer |
| --- | --- |
| 201, 202 and 211 | AMP-01EX Precision Monolithics Incorporated |
| 223 and 212 | LT1054IN8 Linear Technology Corporation |
| 206, 224 and 214 | LP2951CN National Semiconductor Corporation |
| 213 | MC339T Motorola Incorporated |
| 207 | LTC1290 Linear Technology Corporation |
| 208 | REF-43FZ Precision Monolithics Inc. |
| 205 | MAX692MJA Maxim Integrated Products Incorporated |
| 204 | MC68HC68T1P Motorola Incorporated |
| 217 | X28C256D1 Xicor Incorporated |
| 218 | LT1080MJ Linear Technology Corporation |
| 221 | HEF4724BPN Signetics Company |
| 216 | XC68HC811E2FN Motorola Incorporated |

All of the above identified commercially available components require modification with additional circuitry to accomplish their recited functions. Such modifications and circuitry are well within the capability of those of ordinary skill in the technology.

Figure 3:
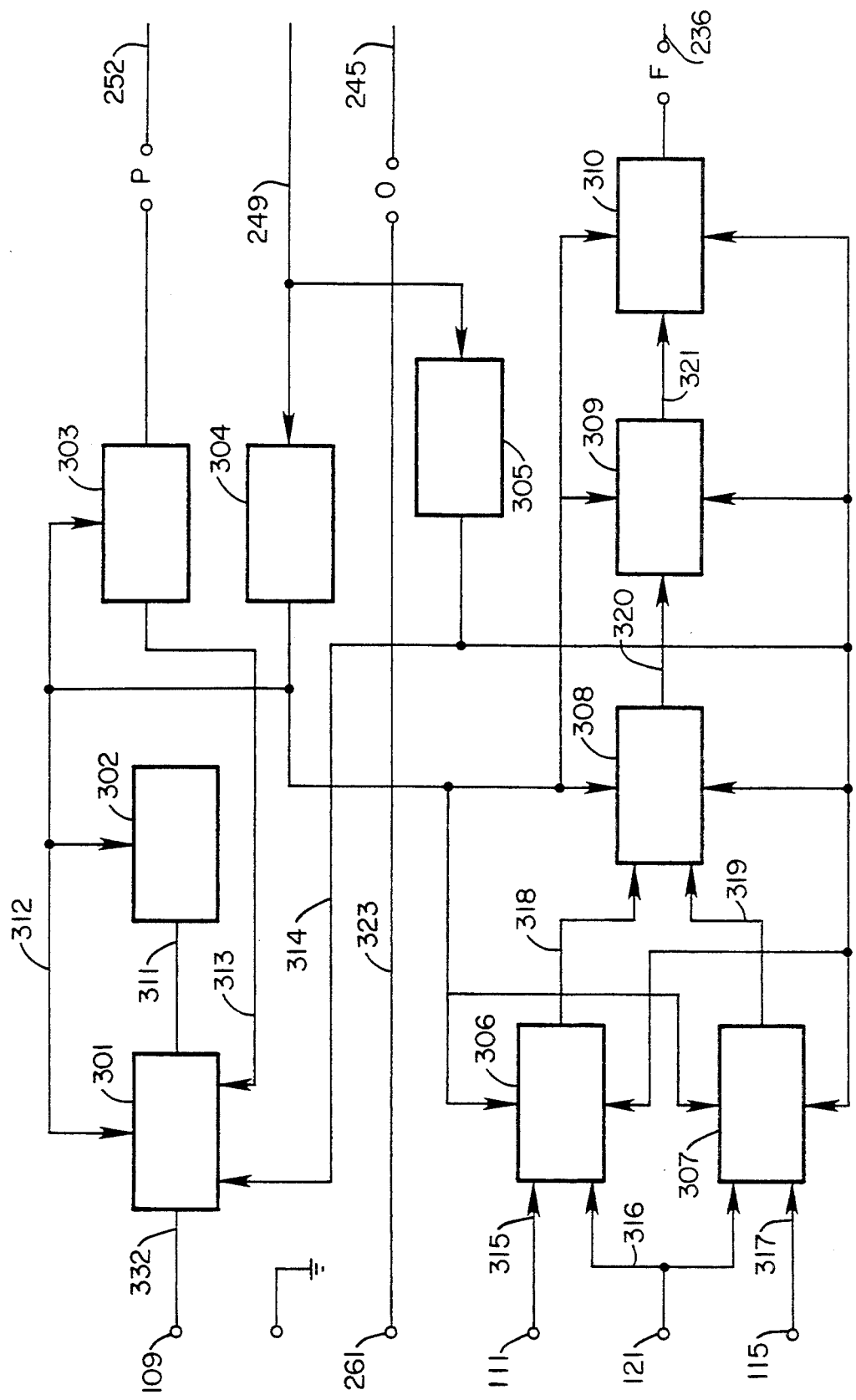
FIG. 3 is a schematic circuit block diagram of the controller board of an ac monitoring system embodying the features of the present invention.

The dual preamp board (see FIG. 3) provides the circuitry to detect and isolate the very small differential signal due to sample sensor resistance changes from the larger common mode signal. The output of the preamp board is an analog voltage which interfaces to the controller board A/D. The previous information describes a direct current (DC) version of the preamp and interface circuit in which a 100 mA DC current is passed through the probe sensors. An alternating current (AC) dual preamp circuit (See FIG. 3) can also be used, passing a single frequency AC signal through the corrosion sensors. A timer circuit 302 generates a fixed frequency, fixed amplitude AC voltage signal 311 which is input to a constant RMS current opamp circuit 301. The constant RMS current circuit will provide a fixed amplitude AC current (preferably less than 0.5 amp.) excitation signal 322 to the probe sensors, regardless of changing loads created by various cable lengths. The resultant AC voltage across the test conductor 315, 316 is amplified through a differential amplifier circuit 306. The AC voltage across the reference element 316, 317 is also amplified by circuit 307. The amplified AC test and reference signals 318, 319 are then compared through an additional differential amplifier 308. The output of this circuit 320 is an AC voltage which represents the difference in electrical resistance between the test conductor and the reference conductor. This signal 320 appears at the same frequency as the timing signal 311 frequency, differing in amplitude and/or phase. The phase-locked loop circuit 309 will then lock onto only signals within a small bandwidth of this desired frequency, thereby rejecting external noise and DC bias components. The output 321 of the phase-locked loop circuit 309 is a DC voltage which is proportional to the amplitude of the AC input signal 320 into the PLL. Proper amplification of this analog voltage 321 through an interface amplifier 310 provides a DC analog voltage for the controller board 12 bit A/D, indicating any difference in electrical resistance between the test sensor and reference sensor of the corrosion probe.

Since the output 321 as amplified by amplifier 310 is a direct current indication of any difference in the electrical resistance between the corrosion probes it is equivalent to the direct current indication from the DC dual preamp circuit of FIG. 2 emitted from the final amplifier 211 (FIG. 2) and provided to A/D converter 207 of the controller board. Accordingly output 321 as amplified by amplifier 310 is provided to such an A/D converter of a corresponding controller board to that described for the embodiment of FIG. 2.

As with the direct current dual preamp board of FIG. 2, power 249 is provided to the dual preamp board by a high-side driver circuit 213 on the controller board. This power input is connected to the preamp voltage converter and voltage regulator. The preamp voltage converter 305 converts the 12 volts supplied by the high-side drive circuit to a −5 volt supply 314 for the amplifiers, constant current, and phase-locked loop circuits. The preamp voltage regulator 304 converts the 12 volt input from the controller board to a +5 ,volt supply 312 for the dual preamp board. As with the direct current dual preamp board, a current enable circuit 303 provides an output signal 313 which turns on the AC current supplied to the probe sensors. Jumper P represents one of four jumpers per preamp board that directs the current control output signal 252 from the controller board. Jumpers 0 and F also function the same on the AC dual preamp board as on the DC board. Jumper O connects the thermistor circuit output 323 to one of eight temperature input channels on the controller board. Jumper F connects the corrosion data signal to its corresponding A/D input on the controller board.

In the application of the method of the present invention to aircraft and in general in areas where the corrosive environment is not severe it is advantageous to utilize very thin sensors. The development of these sensors was required because of the subtle environmental changes which occur in difficult-to-access areas on aircraft. A more accurate measure of these changes is necessary before the corrosiveness of an area can be assessed and/or the level of corrosion on common aircraft alloys can be quantified. Each electrical resistance-type sensor consists of a sensing element and a reference element. Real-time monitoring of the voltage differential between the two elements, which varies in response to corrosion or a reduction in the cross-sectional area of the sensing element is used to determine the corrosiveness of the area being monitored.

Such thin films in the order of one to two mil thickness or less can be achieved on many supporting materials such as glass by known vapor deposition techniques such as sputtering. Ion Beam Enhanced Deposition techniques such as are taught by U.S. Pat. Nos. 4,992,298 and 5,055,318 to Arnold H. Deutchman followed by RF sputtering is contemplated for applying such thin films to plastic surfaces for the construction of sensors such as those described in conjunction with the device of FIG. 1.

Sensors must be fabricated from thin-films of steel and aluminum to optimize CDS performance in areas that are not extremely corrosive. The recommended materials and film thicknesses for aircraft application are Type 1100-0 aluminum alloy (0.0006 in. and/or 0.0012 inch) and AISI 1020 carbon steel (0.003 inch or thinner).

In the experimental use of the method and apparatus of the present invention AISI Type 1100-0 aluminum electrical resistance (ER) sensors were evaluated for three weeks in each of three corrosion environments.

The approximate size of these sensors was 1.5 inches by 1.5 inches. The nominal thicknesses of the elements (sensing and reference) were 0.0012 inch for one sensor and 0.0006 inch for the second sensor. Controlled ion assisted vapor deposition (IAVD) techniques were used to deposit both a 3000 Å thick layer of copper and the above specified thicknesses of aluminum onto a non-conductive 4.0-inch by 4.0-inch by 0.025-inch-thick ceramic substrate. The copper was deposited onto one side of the entire sensor, except in the areas where the aluminum alloy was deposited. Upon the completion of all deposition processing, a photoresist coating was applied over the aluminum sensor patterns. This coating served to protect the aluminum patterns while the copper/aluminum deposit was removed with an etching solution. The resultant patterns remaining on the surface of the ceramic substrate material included multiple sensors, each containing a reference element and sensing element, a temperature compensating element, and five separate electrical connection pads (i.e. conforming to the sensors of FIG. 1).

Five-foot-long, color-coded, No. 26 AWG XET lead wires were then affixed to each sensor's five electrical connection pads (as in FIG. 1) with a conductive epoxy. These connections were then cleaned with a solvent-based cleaner, rinsed with 200-proof ethyl alcohol, conformably coated with a 2-part epoxy (3M No. 2216), and oven cured for 1 hour at 175° F. The reference elements on all sensors were sealed using a 2-part (Uralite 1263 A/B) printed circuit board coating system and allowed to air cure for 48 hours. A minimum of two layers of this coating were applied to these elements prior to testing the sensors.

The non-sensor ends of all of the lead wires were soldered to the appropriate multiple pin connectors, sealed with the 2-part epoxy, and connected to the direct current corrosion diagnostic system unit (CDS) described above in conjunction with FIG. 2. All of the sensors were "tuned" as described below prior to initiating any of the corrosion tests.

Tuning Procedures

The procedures for tuning or "zeroing" the corrosion monitor preamplifier boards includes connecting the appropriate corrosion sensors to each board and setting the instrumentation amplifier offsets to zero for each channel. This procedure sets the offset channel output to zero when the current sources are off. The initial readings with current applied are typically very small when the channels for each sensor are properly tuned. This initial value indicates the difference between the voltage measured across the reference and sensing elements of the sensor. With 100 mA of constant current flowing through the sensing elements, this value actually indicates the relative resistance between the reference and sensing elements. If thicker elements are used (8 mil Al, etc.), the initial values range within 100 and 200 mV of the tuned offset setting. For the thinner sensors tested, especially the 0.6 and 1.2 mil aluminum (ceramic substrate), these values were off as much as $\pm 4$ volts. The exact causes of these offsets have not been determined.

Large offsets may be resolved by setting the zero current offsets to non-zero values. This procedure brings the current-on data points into a more appropriate range. Hence, the CDS units are set to allow preamplifier final outputs of between $-2.5$ and $+2.5$ VDC. Type 1100-0 aluminum sensors were tuned to negative current-on starting points to adjust for any possible sensor asymmetry, and to allow for an increased range over which to measure corrosion. Some sensors provided corrosion data which started as low as $-2$ V and increased to a $+2.5$ V limit, yielding 4.5 V of measurement range.

A difficulty encountered with the experimental sensors was that they caused the amplified voltage signals to go out of range, thus, disabling the preamplifier function. For the thicker Type 7075-T6 sensors, the gain on the preamplifier boards was set to approximately 50,000, meaning that the voltage at the output was approximately 50,000 times the difference between the voltage measured across the sensing and reference elements. With resistance being defined by $R = \delta l/A$, the resistance seen across the sensor elements is directly proportional to the inverse of the cross-sectional area. With the sensor footprint being held constant, the cross-sectional area is directly proportional to the thickness of the aluminum deposited on the ceramic substrate. Therefore, a tenfold reduction in the thickness of the aluminum sensors causes the sensor resistance to be multiplied by a factor of 10. Although the resistance difference between the sensing and reference elements remains relatively small, the larger voltage signals created across the elements cause the instrumentation amplifier inputs to be out of range (above supply limit) before the final data processing stage comparison is complete. For this reason, channel gains for all but one of the experimental aluminum sensors were reduced to approximately 25,000.

CDS Data Interpretation and Processing Procedures

All sensor data was interpreted with respect to its starting value. The information that was downloaded from each CDS unit was processed data. The data collected by the CDS from the individual sensors are equal to the raw current-on data (with noise factor divided out) minus the zero current offset data. The resultant data points ranged between $-2047$ and $+2047$. However, each specific sensor had a total data range of less then 4096. To determine the actual change in resistance of the sensing element: (1) subtract the starting data value (first day of exposure to environment) from the selected measurement interval to obtain overall change, (2) divide the change by 4096/5=819.2 to convert to volts and allow for the 12-bit A/D resolution ($2^{12}=4096$) over the 5 volt range (−2.5 V to +2.5 V), (3) divide the resultant value by the appropriate gain (25,000 or 50,000) to get the actual voltage difference between the reference and sensing elements, and (4) multiply this value by 10 (R=V/I=V/0.1 A=10×V)

Example: Sensor B1, starting value =0.316, interval measurement =1900, gain= ∼50,000

(1) change=1900−(−316)=2216
(2) 2216/819.2=2.705 V
(3) 2.705 V/50,000=54.1 μV
(4) 54.1 E-6×10=541 μΩ

Therefore, assuming the reference element remains protected and unaffected by the corrosive environment, the sensing element of sensor B1 has experienced a 541 μΩ increase in resistance due to corrosion.

To determine the actual data range over which each sensor operates, the initial raw sensor data must be examined. This provides the zero current offset (listed as error on raw data summary) and the data for calculations. The actual data cannot exceed 2047 (raw data=10,235 for a noise factor of 5). Therefore, the total data range is 2047 minus the initial actual data value. The data starting value is determined by subtracting the zero current offset data from the actual initial data.

Example: Sensor B7, raw initial data= −8200, noise factor=5, zero current offset=1350

(1) actual data=raw data/noise factor= −8200/5= −1640
(2) total usable range=2047−(−1640)=3687
(3) starting value= −1640−1350= −2990
(4) maximum data point=2047−zero current offset=2047−1350=697

Therefore, this particular sensor's output data begins at −2990 and will limit or "rail out" at 697.

Modifications to the amplifier and controller circuit boards were required as a result of reducing the thicknesses of the sensing and reference elements on the experimental aluminum sensors. These modifications included a reduction of the gain (25K versus 50K) of the preamplifier circuits. Additional time was required to tune the individual preamplifiers which were connected to the experimental sensors and the sensor with thinner elements.

The three test environments were designed as 1) Rural or Inland Atmosphere (low severity)—Cyclic Temperature/Humidity Test, 2) Industrial Atmosphere (medium severity)—Class III Flowing Mixed Gas (FMG) Test and 3) Marine or Coastal Atmosphere (high severity)—Cyclic Salt Fog/Dry-Air Test.

Each environment was selected to determine if the individual sensors were capable of differentiating between the expected differences in corrosion severity.

An abbreviated description of the testing protocol and actual test conditions used within the three corrosion tests is provided below.

Test Environment No. 1—Cyclic Temperature/Humidity

These tests were performed in an automated Bristol® environmental chamber that was calibrated to alternate cycles of high humidity-hot air and low humidity-hot air. A single 24-hour cycle consisted of 8 hours at 90 percent relative humidity (RH) and 80° F. The CDS unit was programmed to record sensor measurements during both of these intervals throughout the duration of the test. Condensate collection on the surfaces of the test materials was minimized by mounting all sensors and coupons vertically within the cabinet. In addition the individual sensors were isolated from one another to eliminate the possibility of corrosion product cross-contamination.

Test Environment No. 2—Flowing Mixed Gas (FMG)

The FMG corrosion test environment was incorporated into this program because it realistically simulates the kinetics and degradation mechanisms found on metal components after long-term (10 to 15 years) exposures to a polluted industrial indoor environment, similar to an electrical control room. Studies have confirmed that the low levels of gaseous pollutants within the Class III multicomponent FMG laboratory environment are aggressive enough to corrode aluminum and steel materials. The levels of damage varied as a function of sensor materials and exposure time, but it was concluded that the onset and development of corrosion were visually verified on exposed metal within 3 weeks of exposure. Hence, the exposure of steel and aluminum sensors to this environment provided information which was used to quantify the low-level sensitivity and measurement accuracy of the different sensors and/or the CDS package.

The concentrations of the various gaseous pollutants ($Cl_2$, $H_2S$ and $NO_2$) as well as the temperature and relative humidity (RH) levels that were maintained within the environmental chamber throughout the duration of the test exposure are documented in Table 1 below.

Numerous studies in both the laboratory and field have confirmed that a 3-week exposure interval corresponds to a service exposure of approximately 13 years in a polluted industrial indoor environment.

TABLE 1

| Definition of FMG environment by composition | | | | |
|---|---|---|---|---|
| | Gas Concentration, ppb | | | |
| Test/Class | $H_2S$ | $Cl_2$ | $NO_2$ | Relative Humidity, percent | Temp. C. |
| III | 100 | 20 | 200 | 70 | 30 |

For this program, a total of six corrosion sensors and twenty-four weight loss coupons were exposed in the Class III FMG test environment for 3 weeks. The CDS unit was programmed to record and store a single sensor measurement each day through out the scheduled exposure period.

Test Environment No. 3—Salt Fog/Dry-Air

This accelerated corrosion test procedure was selected because it simulates the cyclic effects of wetting and drying the surfaces of materials operating in a coastal or marine environment. The thermal cycling portion of the test is representative of the temperature changes which may occur in the areas on an aircraft that have a frequent exchange of air. However, the concentration of chloride ions in the laboratory test was selected on the basis that it represents a "worst case" scenario of the corrosive conditions that could exist on an aircraft stationed and/or operating in a corrosive marine environment. The higher concentration limits were also required to corrode the test specimen within the short 500-hour exposure period that was used for accelerated laboratory testing.

As with Test No. 1, a total of eight sensors and twenty-four coupons were suspended vertically within the test chamber.

The 24-hour test cycle that was maintained throughout the 3-week test period consisted of an 8 hour exposure to a salt fog that was heated to a temperature of approximately 80° F. At the end of eight hours, the fog was automatically turned off and the chamber was heated with fan-forced, hot, dry air to a temperature of 100° F. for 16 hours. This cycle was selected because it simulates a 2- to 3-year exposure to a warm marine environment. The CDS was programmed to record sensor measurements during both of these intervals to determine the effects of temperature, time-of-wetness, and chlorides on the measurement sensitivity of various sensors. CDS data were compared with the visual examinations that were performed throughout the scheduled test period.

A total of twelve weight loss coupons were removed from the chamber after 1, 2 and 3 weeks of testing.

Figure 4:
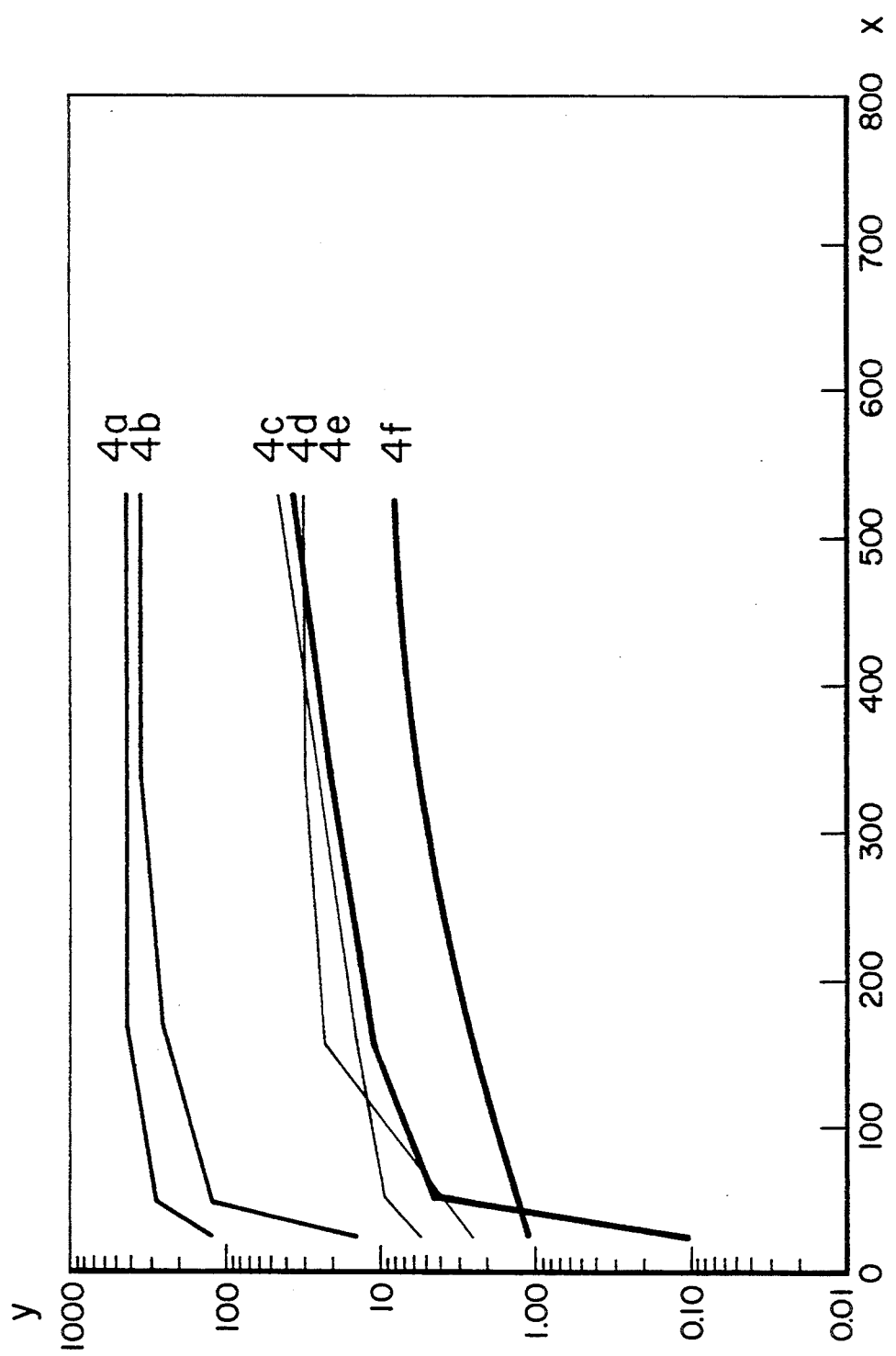
FIG. 4 is a graph showing corrosion test results for thin film aluminum sensors using the process and apparatus of the present invention.

The results of these tests are shown in the graph of FIG. 4. These data reflect the resistance changes (i.e. the voltage changes between the coupon exposed to the test environment and the control coupon) over the plotted periods of time. When compared to weight loss measurements and visual observations these data proved to be a viable means for determining the corrosive effects of the test environments on the coupons.

Figure 5:
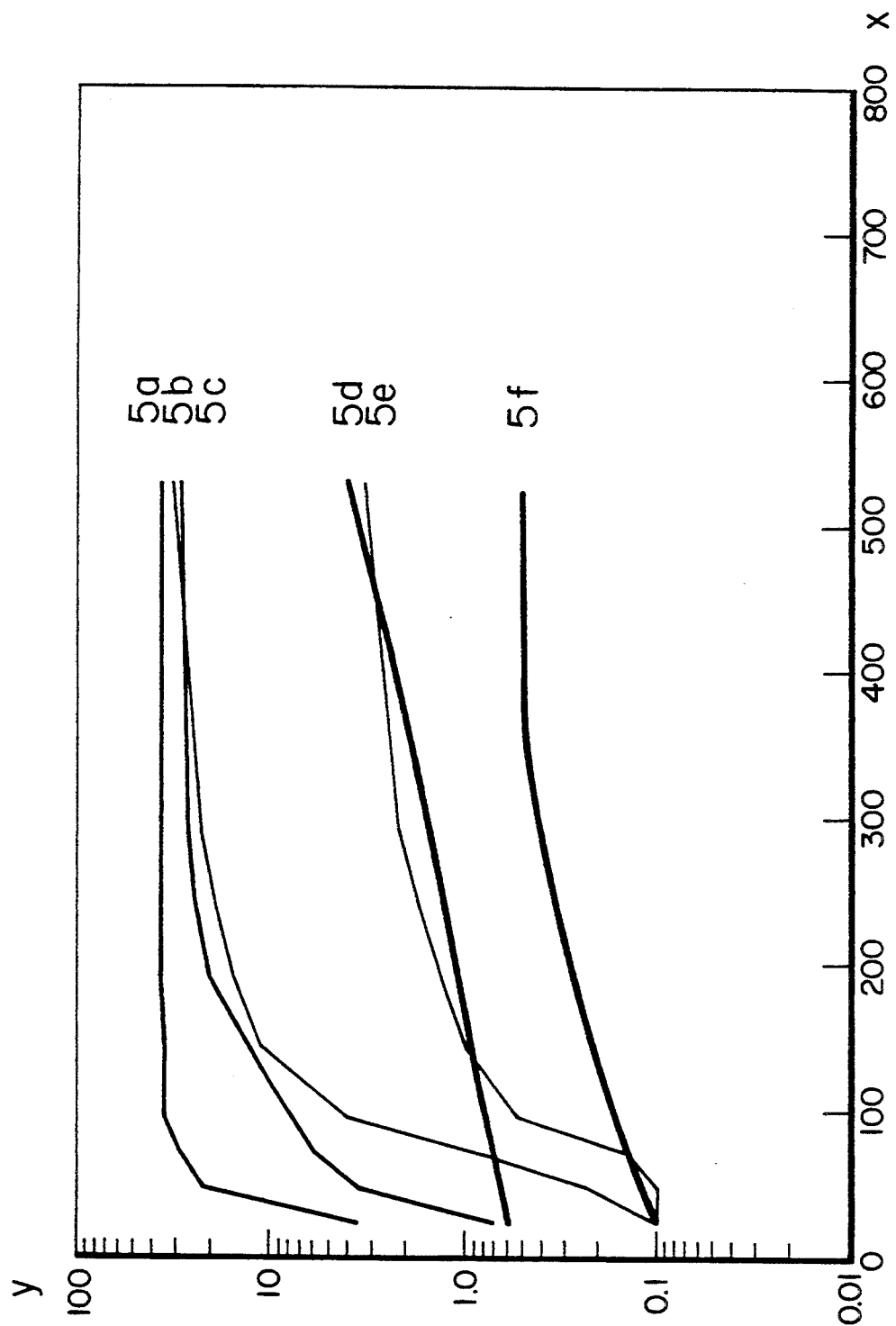
FIG. 5 is a graph showing corrosion test results for thin film steel sensors.
Figure 6:
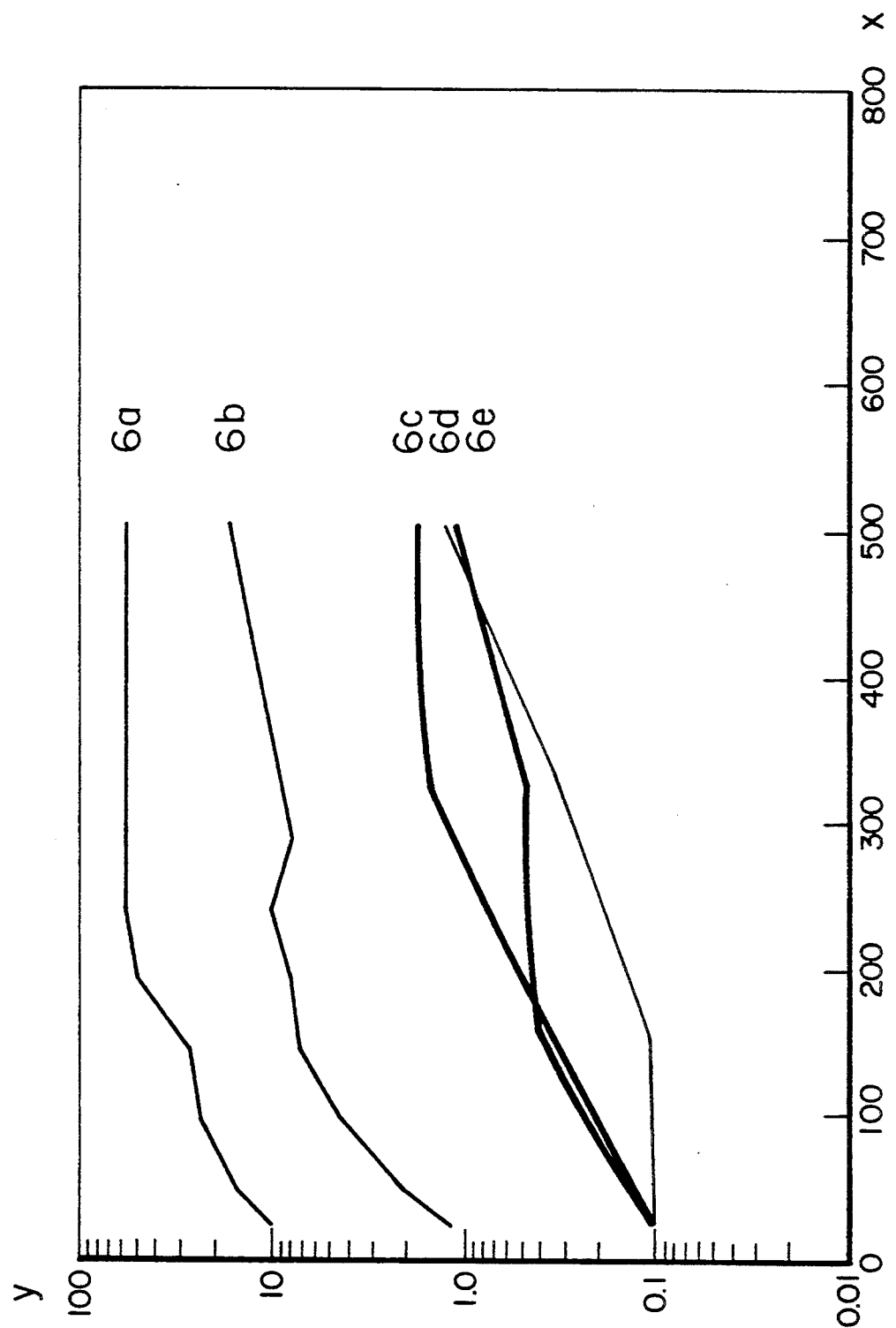
FIG. 6 is a graph showing corrosion test results for thin film Type 7075-T6 aluminum sensors.

Conventional sensors of AISI Type 1020 steel and 7075-T6 aluminum fabricate from conventional metal strip were also CDS tested in the manner described above. The nominal size of these sensors was 1.0 inch × 3.0 inch. The thicknesses of the sensing and reference elements on the 7075-6 aluminum sensors were 0.004 inch and 0.008 inch; whereas, the thickness of the steel elements were 0.003 inch for two sensors and 0.010 inch for two sensors. Post processing techniques and corrosion tests conducted were the same as those described in conjunction of the deposited 1100-0 aluminum. The test results are set forth in graphs of FIGS. 5 and 6 of the drawings.

Having thus described the invention in its preferred embodiment, it will be clear that modifications may be made without departing from the spirit of the invention. Also the language used to describe the inventive concept and the drawings accompanying the application to illustrate the same are not intended to be limiting on the invention. Rather it is intended that the invention be limited only by the scope of the appended claims.

We claim:

1. A method for monitoring material corrosion in a remote area comprising the following steps:
   (a) providing a corrosion sensor having an exposed element disposed for exposure to the environment of said area and a control element protected from said environment;
   (b) imposing an electric current flow through said exposed element and control element from connections remote from said area including a voltage across said exposed element and a separate voltage across said control element;
   (c) separately amplifying the induced voltage of said electric current across said exposed element and across said control element through connections remote from said area;
   (d) measuring the increase in amplified voltage across said exposed element as compared to the amplified voltage across said control element wherein the increase is indicative of the corrosion of said exposed element.

2. The method of claim 1 wherein said current is direct current.

3. The method of claim 2 wherein the current flow of step (b) is about 100 mA, the voltages of step (c) are amplified by approximately a factor of 1000, filtered, and further amplified by approximately a factor of 2.5, and wherein the increase in amplified voltage of step (d) is further amplified by approximately a factor of 20.

4. The method of claim 2 wherein the amplified voltages of step (c) are filtered and further amplified.

5. The method of claim 4 wherein the amplified voltage increase of step (d) is further amplified to enhance the measurement.

6. The method of claim 2 wherein the current flow of step (b) is about 100 mA and the voltages of step (c) are amplified by about 50,000 times before the measurement of step (d).

7. The method of claim 1 wherein the current flow of step (b) is less than 0.5 ampere.

8. The method of claim 1 wherein the voltages of step c) are amplified by from about 20,000 times to about 60,000 times before the measurement of step d).

9. The method of claim 1 wherein the voltages of step c) are amplified by about 50,000 times before the measurement of step d).

10. The method of claim 1 wherein said current is alternating current.

11. The method of claim 10 wherein the amplified voltage increase of step (d) is further amplified to enhance the measurement.

12. The method of claim 1 wherein said exposed and control elements are thin film metal coupons.

13. The method of claim 12 wherein the thickness of said coupons is no greater than about 1 mil.

14. Apparatus for monitoring material corrosion in a remote area comprising:
   (a) a corrosion sensor having an exposed element disposed for exposure to the environment of said area and a control element protected from said environment;
   (b) electric current connections disposed to impose electric current flow through said exposed element and control element from connections remote from said area and to induce a voltage across said exposed element and a separate voltage across said control element;
   (c) one or more amplifiers disposed to separately amplify the voltage induced by said electric current flow across said exposed element and across said control element through connections remote from said area; and
   (d) a voltage measuring device disposed to measure the increase in voltage of the exposed element as compared to the voltage of the control element caused by the corrosive effects of said environment reducing the dimensions of said exposed element so that corrosion of said exposed element may be determined from the voltage increase.

15. The apparatus of claim 14 wherein said electric current connections are disposed to provide direct current.

16. The apparatus of claim 15 wherein said electric current connections are disposed to provide a current of about 100 mA and said one or more amplifiers are disposed to provide total amplification of about 50,000 times.

17. The apparatus of claim 15 including filters for filtering and further amplifying the amplified voltage from said one or more amplifiers.

18. The apparatus of claim 14 including one or more amplifiers for amplifying the amplified voltage increase to enhance such measurements.

19. The apparatus of claim 14 wherein said electric current connections are disposed to provide a current no greater than about 0.5 amperes and the one or more amplifiers are disposed to provide total amplification within the range of 20,000 and 60,000 times.

20. The apparatus of claim 14 wherein said electric current connections are disposed to provide alternating current.

21. The apparatus of claim 14 wherein said exposed and control elements comprise thin film metal coupons having a thickness no greater than about 1 mil.

22. A corrosion monitor system comprising:
(a) a corrosion sensor having an exposed element disposed for exposure to an environment to be monitored and a control element protected from said environment, said exposed and control elements comprising metallic sheets having a thickness no greater than about 1 mil;
(b) electric current connections disposed to impose direct electric current flow through said exposed and control elements and to induce a voltage across said exposed element and a separate voltage across said control element;
(c) one or more amplifiers disposed to separately amplify the voltage induced by said electric current flow across said exposed element and across said control element;
(d) filters for filtering the amplified voltage across said exposed element and the amplified voltage across said control element; and
(e) a voltage measuring device disposed to measure the difference in the amplified and filtered voltage across said exposed element and the amplified and filtered voltage across said control element caused by the corrosive effects of said environment reducing the dimensions of said exposed element so that corrosion of said exposed element may be determined from the voltage difference, said measuring devices being located remote from said sensors.

23. The corrosion monitor system of claim 22 wherein said electric current is direct current.

24. The corrosion monitor system of claim 22 including a battery pack disposed to provide a steady current flow to said elements and power said control system.

* * * * *